United States Patent
Terzopoulos et al.

(10) Patent No.: US 12,198,274 B2
(45) Date of Patent: Jan. 14, 2025

(54) DEEP LEARNING OF BIOMIMETIC SENSORIMOTOR CONTROL FOR BIOMECHANICAL MODEL ANIMATION

(71) Applicant: The Regents of the University of California, Oakland, CA (US)

(72) Inventors: Demetri Terzopoulos, Los Angeles, CA (US); Masaki Nakada, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 375 days.

(21) Appl. No.: 17/618,783

(22) PCT Filed: Jun. 15, 2020

(86) PCT No.: PCT/US2020/037811
§ 371 (c)(1),
(2) Date: Dec. 13, 2021

(87) PCT Pub. No.: WO2020/252484
PCT Pub. Date: Dec. 17, 2020

(65) Prior Publication Data
US 2022/0262075 A1    Aug. 18, 2022

Related U.S. Application Data

(60) Provisional application No. 62/861,911, filed on Jun. 14, 2019.

(51) Int. Cl.
*G06T 19/00* (2011.01)
*A61B 3/00* (2006.01)
(Continued)

(52) U.S. Cl.
CPC .......... *G06T 19/003* (2013.01); *A61B 3/0025* (2013.01); *G06F 30/20* (2020.01); *G06T 7/0012* (2013.01); *G06T 2207/30041* (2013.01)

(58) Field of Classification Search
CPC ................ G06T 19/003; G06T 7/0012; G06T 2207/30041; G06F 30/20; A61B 3/0025
(Continued)

(56) References Cited

U.S. PATENT DOCUMENTS 9,585,631 B2 * 3/2017 Vappou .................. A61B 8/485
10,140,745 B2 * 11/2018 Pai .......................... G06T 13/40
(Continued)

FOREIGN PATENT DOCUMENTS

EP        3984001 A1     4/2022
JP        2007213015 A   8/2007
(Continued)

OTHER PUBLICATIONS

Extended European Search Report for European Application No. 20823697.6, Search completed May 3, 2023, Mailed May 12, 2023, 16 Pgs.
(Continued)

*Primary Examiner* — William D Titcomb
(74) *Attorney, Agent, or Firm* — KPPB LLP (57) ABSTRACT

Systems and methods for training and implementing a sensorimotor control framework in accordance with embodiments of the invention are illustrated. One embodiment includes a method for operating a sensorimotor control framework. The method includes steps for determining a current state of a musculoskeletal model, determining a desired state of the musculoskeletal model, computing a set of muscle activations, based on a difference between the current and desired states, and driving a musculoskeletal model based on the computed muscle activations.

17 Claims, 8 Drawing Sheets
(3 of 8 Drawing Sheet(s) Filed in Color)

(51) Int. Cl.
  *G06F 30/20* (2020.01)
  *G06T 7/00* (2017.01)
(58) Field of Classification Search
  USPC .......................................................... 382/128
  See application file for complete search history.

(56) References Cited

U.S. PATENT DOCUMENTS

| | | | |
|---|---|---|---|
| 11,052,288 B1* | 7/2021 | Berme .................. | A63B 26/003 |
| 11,301,045 B1* | 4/2022 | Berme .................... | G06F 3/016 |
| 11,311,209 B1* | 4/2022 | Berme ................ | A61B 5/1128 |
| 11,501,034 B2* | 11/2022 | De Vries ............... | G06Q 40/08 |
| 2007/0172797 A1 | 7/2007 | Hada et al. | |
| 2008/0221487 A1* | 9/2008 | Zohar .................. | A61B 5/1127 |
| | | | 600/595 |
| 2009/0082701 A1 | 3/2009 | Zohar et al. | |
| 2016/0203630 A1 | 7/2016 | Pai et al. | |
| 2018/0024635 A1 | 1/2018 | Kaifosh et al. | |
| 2018/0336300 A1* | 11/2018 | De Vries ................ | G06F 17/18 |
| 2019/0227627 A1* | 7/2019 | Kaifosh .............. | A61B 5/1128 |
| 2019/0228590 A1* | 7/2019 | Kaifosh .................. | G06F 3/014 |
| 2019/0228591 A1* | 7/2019 | Giurgica-Tiron ...... | G06N 3/044 |
| 2020/0069210 A1* | 3/2020 | Berenzweig ......... | A61B 90/361 |
| 2020/0118350 A1* | 4/2020 | Kaifosh .................. | G06T 19/20 |
| 2020/0125172 A1* | 4/2020 | Kaifosh .................. | G06F 3/017 |
| 2021/0405750 A1* | 12/2021 | Kaifosh .................. | G06F 3/017 |

FOREIGN PATENT DOCUMENTS

| | | |
|---|---|---|
| JP | 2022536349 A | 8/2022 |
| WO | 2020252484 A1 | 12/2020 |

OTHER PUBLICATIONS

International Preliminary Report on Patentability for International Application PCT/US2020/037811, Report issued Dec. 14, 2021, Mailed Dec. 23, 2021, 9 Pgs.
International Search Report and Written Opinion for International Application No. PCT/US2020/037811, Search completed Aug. 12, 2020, Mailed Aug. 31, 2020, 15 Pgs.
Bergstra et al., "Theano: A CPU and GPU Math Compiler in Python", Proceedings of the 9th Python in Science Conference, Austin, Texas, 2010, 7 pgs.
Cruz Ruiz et al., "Muscle-Based Control for Character Animation", Computer Graphics Forum, vol. 36, No. 6, Sep. 2017, pp. 122-147.
Deering, "A Photon Accurate Model of the Human Eye", ACM Transactions on Graphics, vol. 24, No. 3, Jul. 2005, pp. 649-658.
Elgammal et al., "CAN: Creative Adversarial Networks Generating "Art" by Learning About Styles and Deviating from Style Norms", arXiv:1706.07068v1 [cs.AI], Jun. 21, 2017, 22 pgs.
Faloutsos et al., "Composable Controllers for Physics-Based Character Animation", Proceedings of the 28th Annual Conference on Computer Graphics and Interactive Techniques, Los Angeles, California, Aug. 12-17, 2001, 10 pgs.
Fan et al., "Active Volumetric Musculoskeletal Systems", ACM Transactions on Graphics, vol. 33, No. 4, Jul. 2014, Article 152, 9 pgs.
Featherstone, "Rigid Body Dynamics Algorithms", Springer-Verlag Berlin, Heidelberg, 2007, 281 pgs.
Ganin et al., "Synthesizing Programs for Images using Reinforced Adversarial Learning", arXiv:1804.01118v1 [cs.CV], Apr. 3, 2018, 12 pgs.
Gatys, et al., "Image Style Transfer Using Convolutional Neural Networks", In Proceedings of the IEEE Conference on Computer Vision and Pattern Recognition, 2016, pp. 2414-2423.
Geijtenbeek et al., "Flexible Muscle-Based Locomotion for Bipedal Creatures", ACM Transactions on Graphics, vol. 32, No. 6, Article 206, Nov. 2013, 11 pgs.
Goodfellow et al., "Deep Learning", The MIT Press, Cambridge, Massachusetts, 2016, 26 pgs.
Graves, "Generating Sequences With Recurrent Neural Networks", arXiv:1308.0850v1 [cs.NE], Aug. 4, 2013, 43 pgs.
Grzeszczuk et al., "NeuroAnimator: Fast Neural Network Emulation and Control of Physics-Based Models", Computer Graphics Proceedings, Annual Conference Series, Orlando, Florida, Jul. 19-24, 1998, 12 pgs.
Ha et al., "A Neural Representation of Sketch Drawings", arXiv:1704.03477v4 [cs.NE], May 19, 2017, 15 pgs.
He et al., "Delving Deep into Rectifiers: Surpassing Human-Level Performance on ImageNet Classification", Proceedings of the IEEE International Conference on Computer Vision, Santiago, Chile, Dec. 7-13, 2015, pp. 1026-1034.
Hodgins et al., "Animating Human Athletics", Proceedings of SIGGRAPH 95, Aug. 1995, pp. 71-78.
Holden et al., "Phase-Functioned Neural Networks for Character Control", ACM Transactions on Graphics, vol. 36, No. 4, Article 42, Jul. 2017, 13 pgs.
Huang et al., "Full-Body Hybrid Motor Control for Reaching", Proceedings of the 3rd International Conference on Motion in Games, Utrecht, The Netherlands, Nov. 14-16, 2010, pp. 36-47.
Ichim et al., "Phace: Physics-based Face Modeling and Animation", ACM Transactions on Graphics, vol. 36, No. 4, Article 153, Jul. 2017, 14 pgs.
Jackson, "Address in Medicine: On the Comparative Study of Diseases of the Nervous System", The British Medical Journal, vol. 2, Aug. 17, 1889, pp. 355-362.
Jongejan et al., "The Quick, Draw!—AI Experiment", Google, Retrieved from: https://quickdraw.withgoogle.com/, 2016, 1 pg.
Kadlecek et al., "Reconstructing Personalized Anatomical Models for Physics-based Body Animation", ACM Transactions on Graphics, vol. 35, No. 6, Article 213, Nov. 2016, 13 pgs.
Kahler et al., "Head Shop: Generating Animated Head Models with Anatomical Structure", ACM SIGGRAPH Symposium on Computer Animation, Jul. 21, 2002, pp. 55-64.
Kingma et al., "Adam: A Method for Stochastic Optimization", arXiv.org, Retrieved from: https://arxiv.org/abs/1412.6980v1 [cs.LG], Dec. 22, 2014, 9 pgs.
Latash, "The bliss (not the problem) of motor abundance (not redundancy)", Experimental Brain Research, vol. 217, No. 1, Mar. 2012, 5 pgs.
Lee et al., "Comprehensive Biomechanical Modeling and Simulation of the Upper Body", ACM Transactions on Graphics, Aug. 1, 2009, vol. 28, No. 4, pp. 1-17, XP055158375, ISSN: 0730-0301, DOI:10.1145/1559755. 1559756.
Lee et al., "Heads Up! Biomechanical Modeling and Neuromuscular Control of the Neck", ACM Transactions on Graphics, vol. 25, No. 3, Jul. 2006, pp. 1188-1198.
Lee et al., "Locomotion Control for Many-Muscle Humanoids", ACM Transactions on Graphics, vol. 33, No. 6, Nov. 2014, Article 218, 11 pgs.
Lee et al., "Realistic Modeling for Facial Animation", In Computer Graphics Proceedings, Annual Conference Series, Los Angeles, California, Aug. 1995, pp. 55-62.
Lesmana et al., "A biologically inspired controller for fast eye movements", Proceedings of the IEEE International Conference on Robotics and Automation, Shanghai, China, May 9-13, 2011.
Lesmana et al., "Active gaze stabilization", Proceedings of the 2014 Indian Conference on Computer Vision Graphics and Image Processing, Bangalore, India, Dec. 14-18, 2014, No. 81, 8 pgs.
Liu et al., "Learning to Schedule Control Fragments for Physics-Based Characters Using Deep Q-Learning", ACM Transactions on Graphics, vol. 36, No. 3, Article 29, Jun. 2017, 14 pgs.
Monheit et al., "A Kinematic Model of the Human Spine and Torso", IEEE Computer Graphics and Applications, vol. 11, No. 2, Mar. 1991, pp. 29-38.
Nakada, "Deep Learning of Neuromuscular and Sensorimotor Control with Biomimetic Perception for Realistic Biomechanical Human Animation", Dissertation, Jan. 1, 2017, XP055771117, University of California.
Nakada et al., "Deep Learning of Biomimetic Sensorimotor Control for Biomechanical Human Animation", ACM Transactions on Graphics (TOG), Aug. 10, 2018, pp. 1-15, XP055801578, DOI: 10.1145/3197517.3201305.

(56) References Cited

OTHER PUBLICATIONS

Nakada et al., "Deep Learning of Biomimetic Visual Perception for Virtual Humans", Proceedings of the 15th ACM Symposium on Applied Perception, Vancouver, British Columbia, Canada, Aug. 10-11, 2018, Article 20, 8 pgs.

Nakada et al., "Deep Learning of Neuromuscular and Visuomotor Control of a Biomimetic Simulated Humanoid", IEEE Robotics and Automation Letters, IEEE, Feb. 10. 2020, vol. 5, No. 3, pp. 3952-3959, XP011787177, DOI: 10.1109/LFtA.2020.2972829 [retrieved on May 7, 2020].

Nakada et al., "Deep Learning of Neuromuscular Control for Biomechanical Human Animation", International Symposium on Visual Computing, Advances in Visual Computing, Part of the Lecture Notes in Computer Science Book Series, vol. 9474, Dec. 18, 2015, pp. 339-348.

Nakada et al., "Learning Biomimetic Perception for Human Sensorimotor Control", Proceedings of the IEEE Conference on Computer Vision and Pattern Recognition Workshops, 2018, pp. 1917-1922.

Nedel et al., "Anatomic modeling of deformable human bodies", The Visual Computer, vol. 16, No. 6, Oct. 2000, pp. 306-321.

Peng et al., "DeepLoco: Dynamic Locomotion Skills Using Hierarchical Deep Reinforcement Learning", ACM Transactions on Graphics, vol. 36, No. 4, Article 41, Jul. 2017, 16 pgs.

Rabie et al., "Active Perception in Virtual Humans", In Proceedings of the Vision Interface, Montreal, Canada, 2000, 7 pgs.

Sachdeva et al., "Biomechanical Simulation and Control of Hands and Tendinous Systems", ACM Transactions on Graphics, vol. 34, No. 4, Aug. 2015, Article 42, 10 pgs.

Scheepers et al., "Anatomy-Based Modeling of the Human Musculature", Proceedings of the 24th Annual Conference on Computer Graphics and Interactive Techniques, 1997, pp. 163-172.

Scholz et al., "The uncontrolled manifold concept: identifying control variables for a functional task", Experimental Brain Research, vol. 126, No. 3, May 1999, pp. 289-306.

Schwartz, "Spatial Mapping in the Primate Sensory Projection: Analytic Structure and Relevance to Perception", Biological Cybernetics, vol. 25, No. 4, Dec. 1977, pp. 181-194.

Shao et al., "A general joint component framework for realistic articulation in human characters", Proceedings of the 2003 Symposium on Interactive 3D Graphics, Monterey, California, Apr. 27-30, 2003, pp. 11-18.

Si et al., "Realistic Biomechanical Simulation and Control of Human Swimming", ACM Transactions on Graphics, vol. 34, No. 1, Nov. 2014, Article 10, 15 pgs.

Sifakis et al., "Automatic Determination of Facial Muscle Activations from Sparse Motion Capture Marker Data", ACM Transactions on Graphics, vol. 24, No. 3, Jul. 2005, pp. 417-425.

Simhon et al., "Sketch Interpretation and Refinement Using Statistical Models", Proceedings of the 15th Eurographics Conference on Rendering Techniques, Norrköping, Sweden, Jun. 21-23, 2004, 10 pgs.

Sueda et al., "Musculotendon Simulation for Hand Animation", ACM Transactions on Graphics, vol. 27, No. 3, Article 83, Aug. 2008, 8 pgs.

Sun et al., "Robot learns Chinese calligraphy from Demonstrations", Proceedings of the IEEE/RSJ International Conference on Intelligent Robots and Systems, Chicago, Illinois, Sep. 14-18, 2014.

Terzopoulos et al., "Animat vision: Active vision in artificial animals", Proceedings of IEEE International Conference on Computer Vision, Cambridge, Massachusetts, Jun. 20-23, 1995.

Terzopoulos et al., "Physically-Based Facial Modeling, Analysis, and Animation", Journal of Visualization and Computer Animation, vol. 1, No. 2, Dec. 1990, pp. 73-80.

Tresset et al., "Portrait drawing by Paul the robot", Computers & Graphics, vol. 37, No. 5, Aug. 2013, pp. 348-363.

Wang et al., "Optimizing Locomotion Controllers Using Biologically-Based Actuators and Objectives", ACM Transactions on Graphics, vol. 31, No. 4, Article 25, Jul. 2012, 11 pgs.

Wei et al., "Biomechanical simulation of human eye movement", Proceedings of the 5th International Conference on Biomedical Simulation, Phoenix, Arizona, Jan. 23-24, 2010, pp. 108-118.

Wilhelms et al., "Anatomically Based Modeling", Proceedings of the 24th Annual Conference on Computer Graphics and Interactive Techniques, 1997, pp. 173-180.

Yeo et al., "Eyecatch: Simulating Visuomotor Coordination for Object Interception", ACM Transactions on Graphics, vol. 31, No. 4, 2012, pp. 1-10.

Zhang et al., "Drawing and Recognizing Chinese Characters with Recurrent Neural Network", IEEE Transactions on Pattern Analysis and Machine Intelligence, vol. 40, No. 4, Apr. 18, 2017, pp. 849-862.

Zordan et al., "Breathe Easy: Model and control of simulated respiration for animation", Proceedings of the 2004 ACM SIGGRAPH/Eurographics Symposium on Computer Animation, Grenoble, France, Aug. 27-29, 2004, 9 pgs.

\* cited by examiner

DEEP LEARNING OF BIOMIMETIC SENSORIMOTOR CONTROL FOR BIOMECHANICAL MODEL ANIMATION

CROSS REFERENCE TO RELATED APPLICATIONS

This application is a national stage of PCT Patent Application No. PCT/US2020/037811, entitled "Deep Learning of Biomimetic Sensorimotor Control for Biomechanical Model Animation" to Demetri Terzopoulos et al., filed Jun. 15, 2020, which claims priority to U.S. Provisional Application Ser. No. 62/861,911, entitled "Deep Learning of Biomimetic Sensorimotor Control for Biomechanical Model Animation" to Masaki Nakada et al., filed Jun. 14, 2019; the disclosures of which are herein incorporated by reference in their entireties.

FIELD OF THE INVENTION

The present invention generally relates to model animation and, more specifically, biomimetic sensorimotor control for model animation.

BACKGROUND

The modeling of graphical characters based on human anatomy is attracting much attention in computer animation. Increasingly accurate biomechanical modeling of the human body should, in principle, yield more realistic human animation. However, it remains a daunting challenge to control complex biomechanical human musculoskeletal models with over two hundred bones and on the order of a thousand contractile muscle actuators.

Further, the torso, or trunk, is an anatomical term for the central part—in common speech, the core—of many animal bodies, excluding the extremities; i.e., the head and neck and limbs. Although it is indeed of core importance to the human body, the torso has to date received insufficient attention in the computer graphics literature. Biomechanically simulating and controlling the torso, including of course the spine, in its full musculoskeletal complexity, is difficult.

SUMMARY OF THE INVENTION

Systems and methods for training and implementing a sensorimotor control framework in accordance with embodiments of the invention are illustrated. One embodiment includes a method for operating a sensorimotor control framework. The method includes steps for determining a current state of a musculoskeletal model and determining a desired state of the musculoskeletal model. The method further includes steps for computing a set of muscle activations, based on a difference between the current and desired states, and driving a musculoskeletal model based on the computed muscle activations.

In a further embodiment, the current and desired states includes at least one of a position, an orientation, a muscle strain, and a strain rate.

In still another embodiment, the musculoskeletal model is a model of a human being and includes a plurality of Hill-type actuators.

In a still further embodiment, the musculoskeletal model includes a plurality of complexes, computing the set of muscle activations includes computing a first set of muscle activations for a first complex and computing a second set of muscle activations for a second complex.

In yet another embodiment, the plurality of complexes includes at least one of an arm complex, a leg complex, a cervicocephalic complex, and a torso complex.

In a yet further embodiment, computing the second set of muscle activations for the second complex comprises computing forces from the first set of muscle activations, and computing the second set of muscle activations based on the computed forces.

In another additional embodiment, the method further includes steps for receiving sensory inputs from a sensory element, wherein the sensory element is an eye model and the sensory inputs includes a one-dimensional optic nerve vector (ONV).

In a further additional embodiment, the eye model has a non-uniform distribution of photoreceptors on the retina.

One embodiment includes a method for operating a sensorimotor control framework. The method includes steps for determining a current state of a musculoskeletal model includes a torso complex and a set of one or more limb complexes, determining a desired state of the musculoskeletal model, computing forces for the set of limb complexes, computing a set of muscle activations for the torso complex, based on the forces for the set of limb complexes and a difference between the current and desired state of the torso complex, and driving a musculoskeletal model based on the computed muscle activations.

In a further embodiment, computing the set of muscle activations comprises computing a voluntary signal using a voluntary controller, computing a reflex signal using a reflex controller, and computing the set of muscle activations based on outputs from the voluntary controller and outputs from the reflex controller.

In still another embodiment, the voluntary controller takes as input a target orientation and output activations for muscles of an associated muscle group.

In a still further embodiment, the reflex controller takes as input muscle strains and strain rates of muscles of an associated muscle group.

One embodiment includes a method for training a torso controller of a torso complex. The method includes steps for receiving training data includes a set of target inputs and a target state, determining forces exerted by limb complexes attached to the torso complex, computing muscle activations for the torso complex based on the target inputs, the target state, and the determined forces, computing differences between a result of the muscle activations and the target state, and modifying parameters of the torso controller based on the differences between the target and current states.

In yet another embodiment, the method further includes steps for synthesizing the training data.

In a yet further embodiment, synthesizing the training data comprises specifying a current position and a target position for a model, determining discrepancies between the current position and the target position, determining muscle activation adjustments based on the discrepancies and muscle activations of the current position, determining discrepancies includes solving an inverse kinematics problem.

In another additional embodiment, the discrepancies includes at least one of an angular discrepancy, a linear discrepancy, and an acceleration discrepancy.

In a further additional embodiment, determining muscle activation adjustments includes performing a muscle optimization technique to compute the minimal muscle activations that can generate a desired torque.

In another embodiment again, synthesizing the training data comprises specifying current and desired muscle strains and strain rates for a model, determining changes in muscle strain and in strain rate for muscles of the controlled group, and determining muscle activation adjustments based on the changes in muscle strain and in strain rate.

In a further embodiment again, determining forces exhibited by limb complexes includes computing random forces for the set of limb complexes by sending activation signals to the limb complexes.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description and claims will be more fully understood with reference to the following figures and data graphs, which are presented as exemplary embodiments of the invention and should not be construed as a complete recitation of the scope of the invention.

DETAILED DESCRIPTION

Systems and methods in accordance with a variety of embodiments of the invention provide a biomimetic sensorimotor control framework that can be used to control and animate a model. Biomimetic sensorimotor control frameworks in accordance with many embodiments of the invention can process sensory information and provide musculoskeletal controls to a model. In several embodiments, biomimetic sensorimotor control frameworks can include a comprehensive, anatomically-accurate, muscle-actuated biomechanical human model, as well as a sensorimotor control system.

Human models in accordance with many embodiments of the invention can include a biomechanically simulated human musculoskeletal model actuated by numerous muscles. In some embodiments, systems and processes can provide a whole-body biomechanical human model with a full set of articular degrees of freedom actuated by many hundreds of muscles. In a number of embodiments, models can employ a biomimetic vision system, including foveated retinas in human-like eyes capable of realistic eye movements. Ray tracing serves in computing the irradiance captured by a biologically-inspired non-uniform distribution of photoreceptors on the retina. In certain embodiments, simulated models can include with eyes whose retinas have non-uniformly distributed photoreceptors.

Sensorimotor control systems in accordance with a number of embodiments of the invention can include a number of subsystems, such as (but not limited to) a sensory subsystem and a neuromuscular motor subsystem. In some embodiments, each subsystem is composed of a number of trained machine learning models or networks (e.g., deep neural networks (DNNs). Neuromuscular motor subsystems in accordance with a variety of embodiments of the invention can include controllers (or DNNs) that control the actuation of muscles in an area of the body. In numerous embodiments, controllers can include voluntary and reflex networks that can be used to produce muscle activations for desired motions and balancing reflexes.

In some embodiments, trained networks of the sensorimotor control system can be trained with large quantities of training data synthesized by the biomechanical human musculoskeletal model itself. Training networks in accordance with a variety of embodiments of the invention can include synthesizing training data based on a biomechanical human musculoskeletal model simulator. Motor controllers in accordance with certain embodiments of the invention can be trained to produce muscle activation adjustments based on current muscle activations and discrepancies between a current position and a target position of a body part. In various embodiments, reflex controllers can be trained to produce muscle-stabilizing signals based on input muscle strains and strain rates.

Human Model

Figure 1:
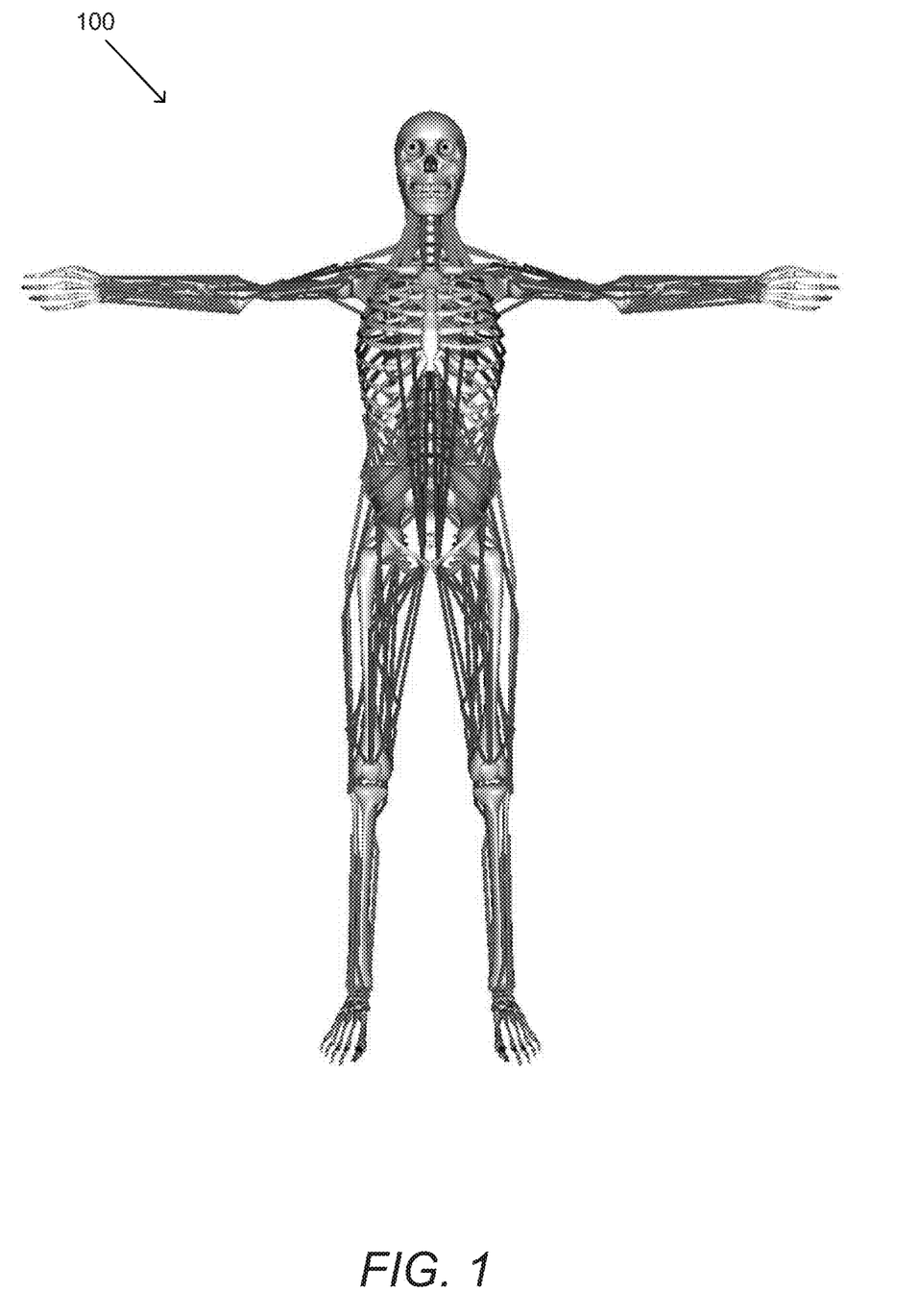
FIG. 1 illustrates an example of a biomechanically simulated human musculoskeletal model.

An example of a biomechanically simulated human musculoskeletal model is illustrated in FIG. 1. In this example, the model 100 includes 193 bones and 823 Hill-type muscle actuators. In some embodiments, each skeletal muscle is modeled as a Hill-type uniaxial contractile actuator that applies forces to the bones at its points of insertion and attachment. Although a specific example of a biomechanically simulated human musculoskeletal model is discussed above, many musculoskeletal models can be implemented in accordance with many different embodiments of the invention. For example, although many of the examples described herein are described with reference to a human model, one skilled in the art will recognize that similar processes can be applied to musculoskeletal models of other types of animals. It is therefore to be understood that the present invention may be practiced in ways other than specifically described, without departing from the scope and spirit of the present invention.

In certain embodiments, a human model also includes eyes that are modeled to see like a human eye. Eye models in accordance with numerous embodiments of the invention are modeled as an ideal pinhole camera. In certain embodiments, eye models can include a finite-aperture pupil that dilates and constricts to accommodate to the incoming light intensity. Eye models in accordance with many embodiments of the invention can include cornea and lens components to refract light rays and can be capable of adjusting the optical depth of field through active, ciliary muscle control of the lens deformation. In numerous embodiments, eye models are purely kinematic rotating spheres. Eye models in accordance with a variety of embodiments of the invention can be biomechanical, actuated by extraocular muscles, including four rectus muscles and two oblique muscles to induce torsion movements around the gaze direction.

To emulate biomimetic foveated vision, eye models in accordance with many embodiments of the invention position the photoreceptors on the hemispherical retina according to a noisy log-polar distribution, which has greater biological fidelity compared to earlier foveated vision models. In various embodiments, photoreceptors can be placed in slightly different positions on the two retinas.

In numerous embodiments, foveated retinal RGB images captured by each eye are output for further processing down the visual pathway, not as a 2D array of pixels, but as a 1D vector, referenced herein as an Optic Nerve Vector (ONV). ONVs in accordance with certain embodiments of the invention have a length based on the number of photoreceptors in the eye and a number of layers (e.g., colors) for each photoreceptor. For example, in the case where an eye has 3,600 photoreceptors and three layers, an ONV could have length 10,800 (3,600*3=10,800). The raw sensory information encoded in ONVs in accordance with a variety of embodiments of the invention can feed the vision networks that directly control eye movements and/or the neuromuscular motor controller networks that orchestrate neck-actuated head motions and the actions of the limbs. In various embodiments, ONVs are used to construct 2D retino-cortical maps from the 1D retinal ONV outputs.

In various embodiments, human models can also include a vestibular system emulating that of the human inner ear and related neural circuits. Human models in accordance with some embodiments of the invention can utilize trained neural controllers that appropriately couple head orientation to eye movement through a Vestibulo-Ocular Reflex (VOR).

Sensorimotor Control System

Figure 2:
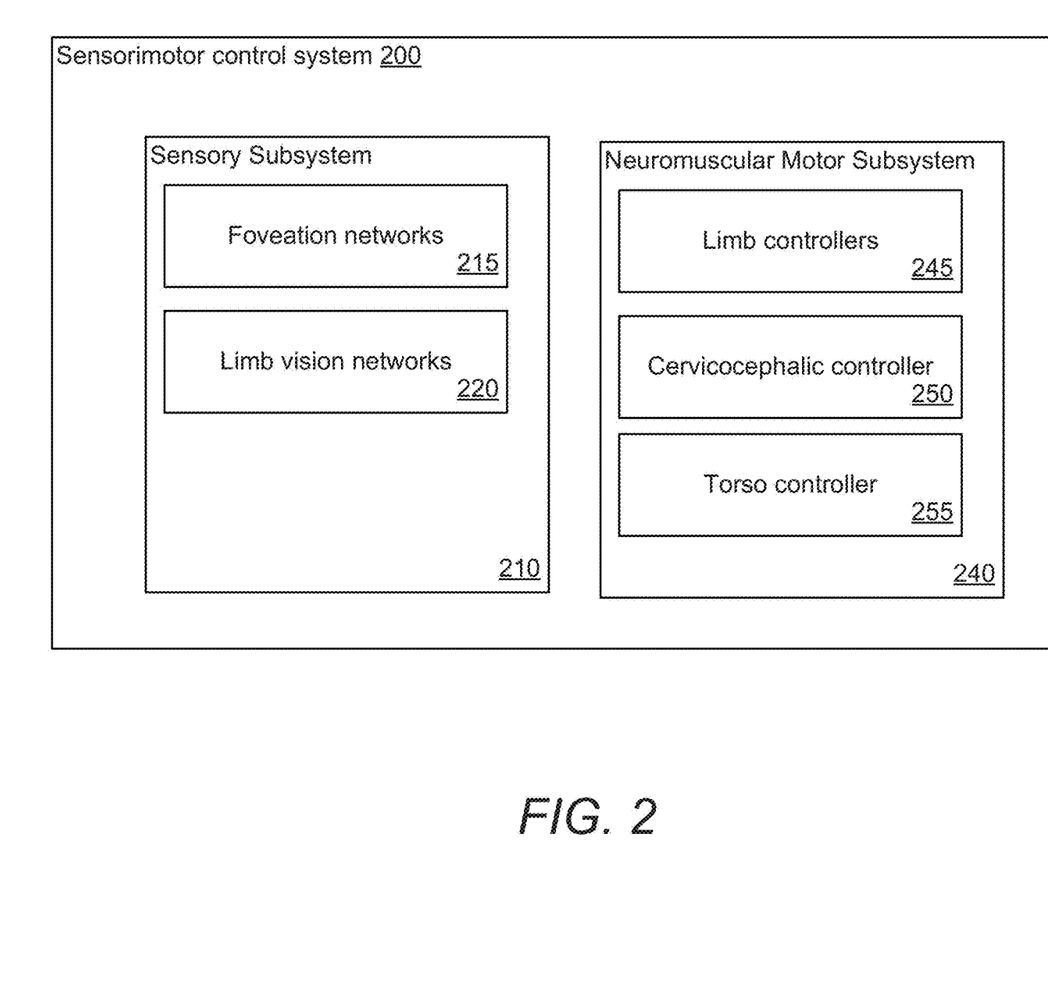
FIG. 2 illustrates an example of a sensorimotor control system in accordance with an embodiment of the invention.

An example of a sensorimotor control system in accordance with an embodiment of the invention is illustrated in FIG. 2. Sensorimotor control systems can be used to sense, move, and react within an environment. Sensorimotor control system 200 includes sensory subsystem 210 and neuromuscular motor subsystem 240.

Sensory subsystems in accordance with many embodiments of the invention can be used to sense (e.g., see, hear, feel, etc.) an environment and/or objects within the environment. In a number of embodiments, sensory subsystems can drive eye and head movements and/or extract visual information required to direct arm and leg actions directly from photoreceptor responses from eyes of a model. Neuromuscular motor subsystems in accordance with a variety of embodiments of the invention can be used to activate and control the muscles and movements of a model based on the sensed environment, as well as on other inputs and/or instructions that may be received by the model.

In some embodiments, sensory subsystems can include foveation and limb vision networks that interpret the sensory information provided by eyes of a human model (e.g., via a 10,800-dimensional ONV). In this example, sensory subsystem 210 includes foveation networks 215 and limb vision networks 220.

Foveation networks in accordance with a variety of embodiments of the invention can be used for tracking objects within view of a model's eyes by moving the model's eyes and/or head. Sensory subsystems in accordance with some embodiments of the invention include left and right foveation networks that can operate to produce voluntary changes in gaze direction by driving saccadic eye movements to foveate visible objects of interest, thereby observing them with maximum visual acuity. The maximum speed of saccadic eye movements is 900 degrees/sec, and the eye almost instantly rotates to foveate the visual target. To aid foveation, fixation, and visual tracking, eye movements induce compensatory head movements, albeit much more sluggish ones due to the considerable mass of the head. Hence, foveation networks in accordance with various embodiments of the invention can also operate to control head movements, by driving a cervicocephalic neuromuscular voluntary motor network. In several embodiments, cervicocephalic neuromuscular voluntary motor networks can be driven by an aggregate (e.g., an average) of the outputs of left and right foveation networks. In certain embodiments, foveation networks are tapered, fully-connected DNNs, with input layers having a number of units (e.g., 10,800) in accordance with the dimensionality of the ONV, and an output layer with units representing eye rotation adjustments, $\Delta\theta$ and $\Delta\phi$. Given its ONV input, the desired output of a foveation network can be the angular discrepancies, $\Delta\theta$ and $\Delta\phi$, between the actual gaze directions of the eyes and the known gaze directions that would foveate the sphere.

Limb vision networks in accordance with some embodiments of the invention can feed into controller networks to control the movements and muscles of a human model. In several embodiments, sensory subsystems include separate limb vision networks for each limb (e.g., right arm, left arm, right leg, left leg, etc.). Left and right limb (arm and leg) vision networks in accordance with some embodiments of the invention can be used to estimate the separation in 3D space between the position of the end effector (hand or foot) and the position of a visual target, thus driving the associated limb neuromuscular motor controller to extend the limb to touch the target. In certain embodiments, limb vision networks can estimate arm-to-target 3D discrepancies, $\Delta x$, $\Delta y$, and $\Delta z$, that drive limb actions via the limb neuromuscular motor controllers. Sensory subsystems in accordance with many embodiments of the invention can include an Opto-Kinetic Reflex (OKR) that utilize trained neural networks. In various embodiments, the architecture of the limb vision network is identical to the foveation network, except for the size of the output layer, which has 3 units, $\Delta x$, $\Delta y$, and $\Delta z$, the estimated discrepancies between the 3D positions of the end effector and visual target.

Neuromuscular motor subsystem 240 of this example includes limb controllers 245, cervicocephalic controller 250, and torso controller 255. Neuromuscular motor subsystems in accordance with a number of embodiments of the invention can include control networks (or controllers) to achieve neuromuscular control. In many embodiments, controllers can include a set of networks trained to produce muscle activation signals for a muscle group in order to position the model in a desired orientation. In some embodiments, multiple controllers are used for separate muscle groups, such as (but not limited to) the cervicocephalic complex, the limb complexes (e.g., arms and legs), and/or the torso complex. In several embodiments, controllers can be driven by an aggregate (e.g., an average) of the outputs of limb vision networks. Alternatively, or conjunctively, a particular controller can be driven by specific limb vision network specifically trained for the particular controller, without further input from other limb vision networks.

For example, neuromuscular motor subsystems in accordance with a number of embodiments of the invention can include control networks to control the 216 neck muscles that actuate the cervicocephalic musculoskeletal complex to produce natural head movements, and other control networks to control each limb, e.g., the 29 muscles of each arm and 39 muscles of each leg. In several embodiments, neuromuscular controllers in a motor subsystem can include a neuromuscular control network (or controller) for one or more complexes (e.g., cervicocephalic, limbs, core, etc.) of a human model.

Controllers for the core musculoskeletal complex in accordance with some embodiments of the invention can be trained to work in concert with neuromuscular controllers specialized to the five extremities—the cervicocephalic, two arm, and two leg musculoskeletal complexes. In several embodiments, the deep neuromuscular controller of the torso takes into consideration the interaction caused by the co-variation between the torso and the extremities resulting in natural, realistic whole-body human animation.

Figure 3:
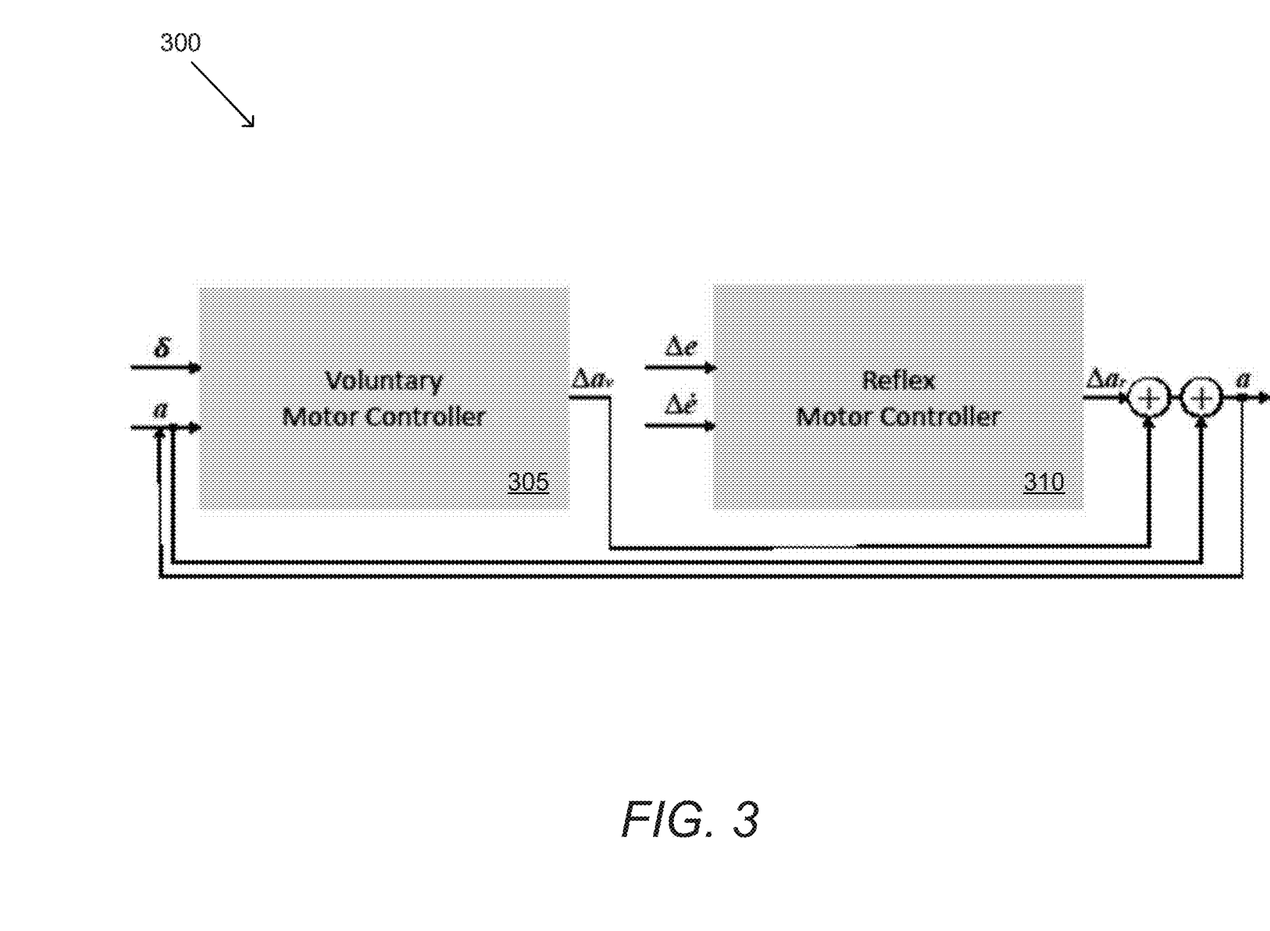
FIG. 3 illustrates an example architecture of a neuromuscular controller in accordance with an embodiment of the invention.

An example architecture of a neuromuscular controller in accordance with many embodiments of the invention is illustrated in FIG. 3. Neuromuscular motor controller architecture 300 includes a voluntary controller 305 and a reflex controller 310. In this example, muscle activation signal a feeds back as an input to voluntary controller 305, making the neuromuscular controller 300 a recurrent neural network. In numerous embodiments, both voluntary and reflex controllers can be trained networks (e.g., DNNs) that produce muscle activation adjustment ($\Delta$) signals.

Voluntary controllers in accordance with many embodiments of the invention can be used to control muscle groups to perform various functions for a model. For example, cervicocephalic voluntary motor networks in accordance with some embodiments of the invention can generate efferent activation signals to the neck muscles in order to balance the mass of the head in gravity atop the flexible cervical column while actuating realistic head movements to achieve target head poses. In numerous embodiments, the function of the 4 limb voluntary motor networks is to generate efferent activation signals to the muscles of the four limbs in order to execute controlled arm and leg movements, such as extending a limb to reach a target. The function of the torso voluntary motor network in accordance with many embodiments of the invention is to generate efferent activation signals to the torso muscles in order to balance the mass of the trunk in gravity atop the flexible spinal column while actuating realistic torso movements to achieve target trunk poses that serve the purposes of the arms and head.

In many embodiments, voluntary controllers for each muscle group take, as input, a target orientation and/or position, and output activations for muscles of the associated muscle group. Voluntary controllers in accordance with a variety of embodiments of the invention take a target discrepancy $\delta$ and, recurrently, muscle activations a as inputs. In a number of embodiments, voluntary controllers can produce signals $\Delta a_v$, which can induce the desired actuation of the associated musculoskeletal complex.

In several embodiments, the architecture of the voluntary motor networks for all of the different complexes is identical, except for the sizes of the input and output layers. The input layers of voluntary motor networks in accordance with some embodiments of the invention include units that represent the (angular or linear) components of the discrepancy between the value of some relevant feature of the virtual human's state, such as head orientation or hand/foot position, and the target value of that feature, as well as units that represent the current activations, $a_i(t)$, for $1 \leq i \leq n$, of each of the n muscles in the associated musculoskeletal complex. The output layer in accordance with several embodiments of the invention can include units that encode the adjustments $\Delta a_i(t)$, for $1 \leq i \leq n$, to the muscle activations, which can then contribute additively as $a_v$ to updating the muscle activations.

Reflex controllers in accordance with certain embodiments of the invention can take the changes in muscle strains e and strain rates ė as inputs. In a variety of embodiments, reflex controllers can produce muscle-stabilizing signals $\Delta a_r$. The outputs of neuromuscular motor controllers in accordance with a variety of embodiments of the invention can be given by $a(t+\Delta t)=a(t)+(\Delta a_v(t)+\Delta a_r(t))$.

The reflex muscle activation signals are $a_r=k_p(e^d-e)+k_d \text{sat}_m(\dot{e}^d-\dot{e})$, where e and ė are the current muscle strain and strain rates, and $e^d$ and $\dot{e}^d$ are the desired strain and strain rates, respectively, and where the saturation function $$\text{sat}_m(x) = \begin{cases} x & |x| < m; \\ m\,\text{sgn}(x) & \text{otherwise} \end{cases}$$

avoids instability from overly large derivative feedback. In a variety of embodiments, the desired strain and strain rates can be computed by the setpoint method. In certain embodiments, the input is the concatenation of the desired adjustment of the strain $\Delta e = e^d - e$ and strain rate $\Delta \dot{e} = \dot{e}^d - \dot{e}$, while the desired output of the network in response to the input is the reflex activations adjustment $\Delta a_r$, which can be added to the neuromuscular controller output.

Processes in accordance with numerous embodiments of the invention can iteratively update the joint angles in a gradient descent manner such that the difference between the current pose q and target pose q* is minimized. In many embodiments, controllers can determine the required accelerations to reach the target at each time step h using the following PD approach:

$$\ddot{q}^* = k_p(q^*-q) + k_d(\dot{q}^*-\dot{q}),$$

with proportional gain $$k_p = \frac{2(1-\gamma)}{h^2},$$

where $\gamma$ is me error reduction rate, and derivative gain $k_d = 2/h$.

Processes in accordance with some embodiments of the invention implement a hybrid recursive dynamics algorithm, which makes it possible to compute the desired accelerations for acceleration-specified joints and the desired torques for torque-specified joints. In various embodiments, processes can set the muscle-driven joints as acceleration-specified joints, while the passive joints remain torque-specified joints. Desired accelerations for the muscle-driven joints can be computed and a hybrid dynamics algorithm can be run to compute the resulting accelerations for the passive joints. In a number of embodiments, the system can be advanced to the next time step using a first-order implicit Euler method, and the hybrid dynamics algorithm can be used to compute torques for the muscle-driven joints, thus obtaining the desired torques for the muscle-driven joints and accelerations for the passive joints. After the desired torques are obtained, an optimization problem for agonist and antagonist muscles can be solved to compute the desired minimal-effort muscle activation levels.

Training

Training processes in accordance with numerous embodiments of the invention incorporate an online, continual, deep reinforcement learning scheme, which could give a model the ability to learn continuously from its experience. Such a learning process can be especially important for motions that come with clear objectives such as playing sports, which humans continuously practice to improve their skills. In various embodiments, training data is synthesized offline using a biomechanical human musculoskeletal model simulator. Once they are trained, networks can quickly produce the required muscle activation signals online.

Figure 4:
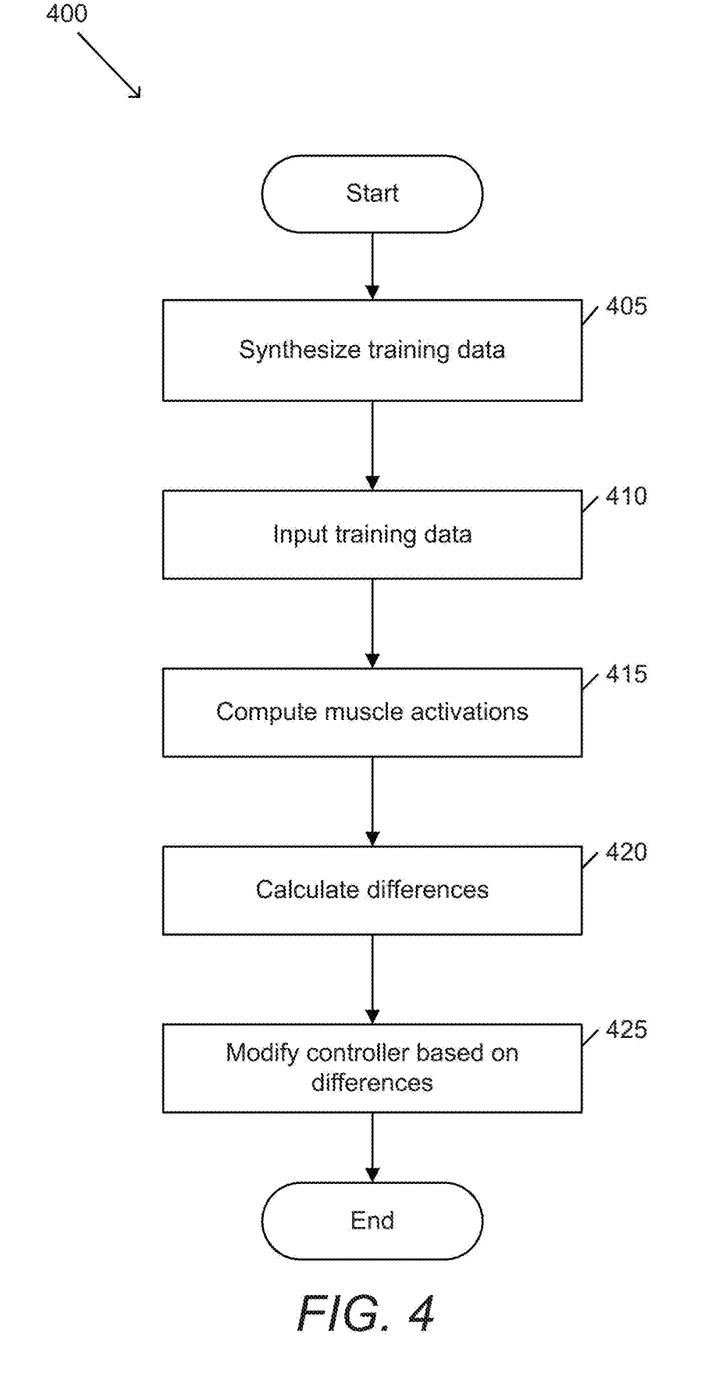
FIG. 4 conceptually illustrates an example of a process for training controllers in accordance with an embodiment of the invention.

An example of a process for training controllers in accordance with an embodiment of the invention is conceptually illustrated in FIG. 4. Process 400 synthesizes (405) training data. Synthesizing training data in accordance with a variety of embodiments of the invention can be performed using a biomechanically simulated human musculoskeletal model. Training data in accordance with numerous embodiments of the invention can include (but is not limited to) position discrepancies, changes in muscle strain, changes in strain rate, current state, desired state, forces from other complexes, and/or muscle activations. Example processes for synthesizing training data are described below with reference to FIGS. 5 and 6.

Process 400 inputs (410) the training data to a controller (e.g., a reflex or voluntary motor controller) and computes (415) muscle activations based on the input data. Process 400 calculates (420) differences between the computed muscle activations and the desired muscle activations from the training data. Process 400 modifies (425) the controller based on difference between determined muscle activation and computed activations. In several embodiments, controllers are deep neural networks that can be trained through a backpropagation process that adjusts weights of the neural network.

Although specific methods of training controllers of a sensorimotor control system are discussed above, many methods can be implemented in accordance with many different embodiments of the invention. It is therefore to be understood that the present invention may be practiced in ways other than specifically described, without departing from the scope and spirit of the present invention.

In certain embodiments, processes for training and utilizing motor and reflex networks are largely similar, but are based on different sets of inputs. Voluntary motor control networks in accordance with many embodiments of the invention are trained on n+k inputs, where n is the number of muscles being controlled and k are a number of discrepancies. Each of the n muscles can provide a current muscle activation for the input. Discrepancies in accordance with a number of embodiments of the invention can include linear and/or angular discrepancies that are calculated between a current position (or orientation) and a target position. Reflex control networks in accordance with various embodiments of the invention are trained on 2n inputs. Inputs for training reflex control networks in accordance with some embodiments of the invention include changes in muscle strain and in strain rate for each of the n muscles of the controlled complex.

As described above, sensorimotor control systems in accordance with a number of embodiments of the invention can be trained based on synthesized training data. Examples of synthesizing training data for voluntary and reflex controllers are described below with reference to FIGS. 5 and 6. By repeatedly specifying a series of random target positions and actuating the limb to reach them, processes in accordance with certain embodiments of the invention can generate large training datasets of input-output pairs to train each of the voluntary and reflex motor controllers.

Figure 5:
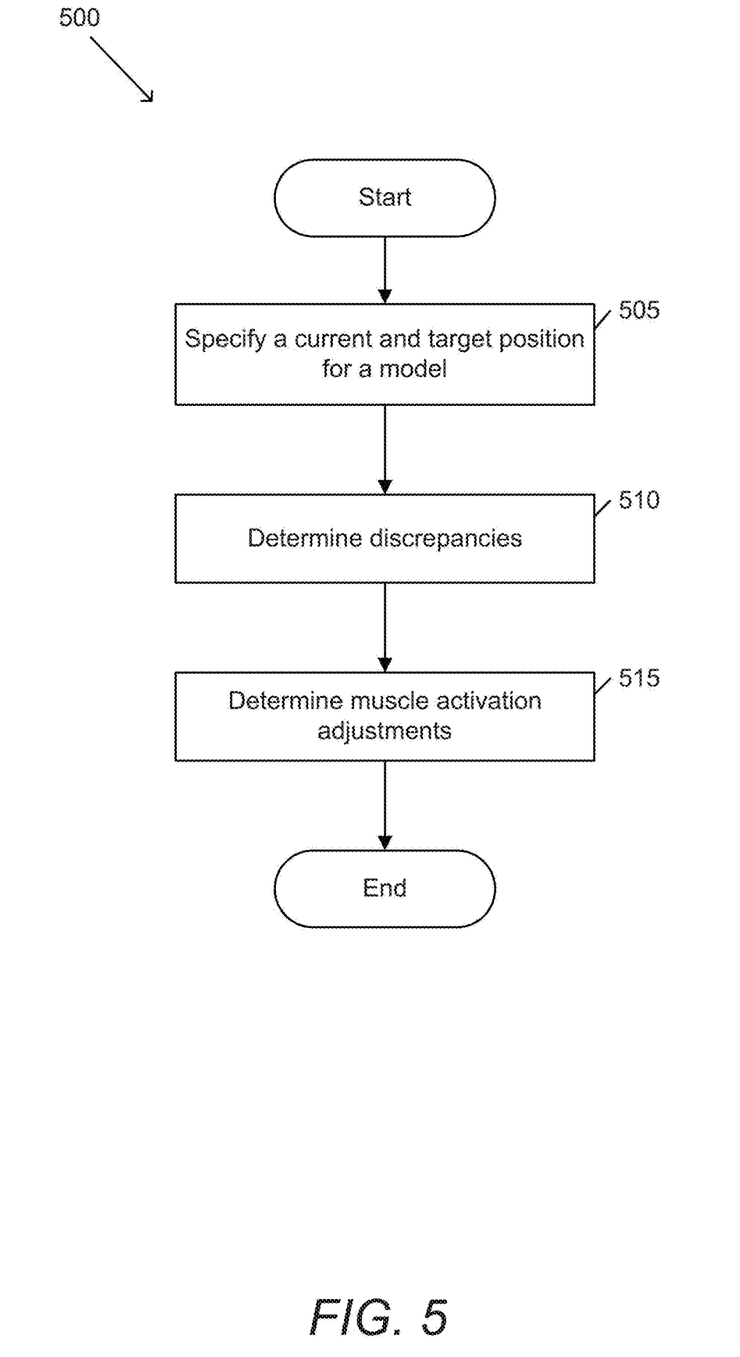
FIG. 5 conceptually illustrates an example of a process for synthesizing training data for a voluntary controller in accordance with an embodiment of the invention.

An example of a process for synthesizing training data for a voluntary controller in accordance with an embodiment of the invention is conceptually illustrated in FIG. 5. Process 500 specifies (505) a current and target position for a model. The positions (or pose) for the model can include (but is not limited to) a position of an extremity, an orientation of the head, etc. Process 500 determines (510) discrepancies between the current position and a target position. Target positions can be determined based on a desired pose, an objective to be accomplished, etc. Discrepancies can include (but are not limited to) angular discrepancies (e.g., in an orientation of the head) and linear discrepancies (e.g., linear distances within 3D space). In certain embodiments, discrepancies for a joint or body part can be computed by solving an inverse kinematics problem. In numerous embodiments, desired accelerations for the joints can be computed to achieve the desired motion in a given time step. Joint torques required for a motion can be computed in accordance with some embodiments of the invention by solving the inverse dynamics problem for each joint, subject to external forces such as gravity.

Process 500 then determines (515) muscle activation adjustments based on the discrepancies and current muscle activations of the model. In numerous embodiments, muscle activation adjustments can be determined through a muscle optimization technique that can be applied to compute the minimal muscle activations that can generate the desired torque for each joint; i.e, a minimal-effort objective. Synthesized training data for a voluntary controller in accordance with a variety of embodiments of the invention can include model state (e.g., position, orientation, etc.), discrepancies, and muscle activation adjustments that are computed based on a simulated model.

Figure 6:
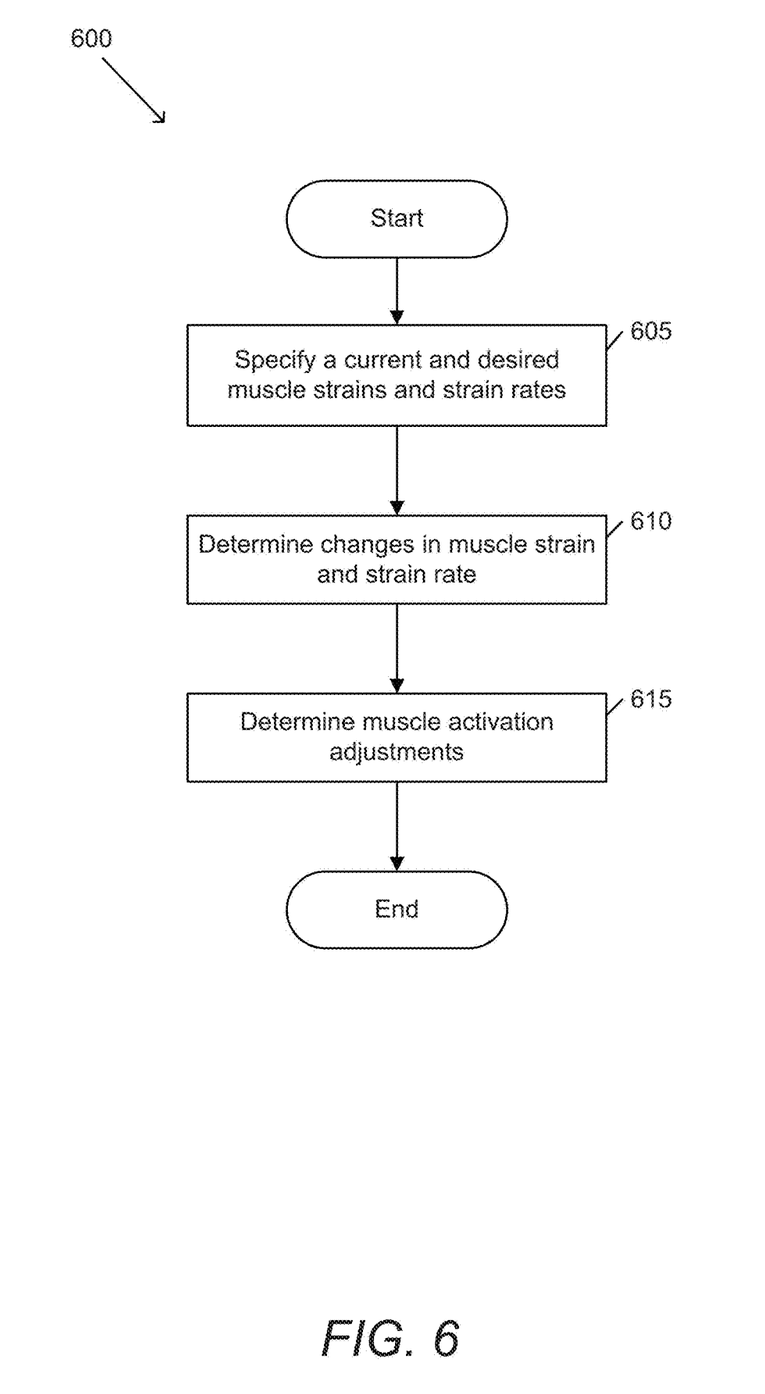
FIG. 6 conceptually illustrates an example of a process for synthesizing training data for a reflex controller in accordance with an embodiment of the invention.

An example of a process for synthesizing training data for a reflex controller in accordance with an embodiment of the invention is conceptually illustrated in FIG. 6. Process 600 specifies (605) current and desired muscle strains and strain rates for a model. Desired strain and strain rates in accordance with many embodiments of the invention can be computed by a setpoint method. Process 600 determines (610) changes in muscle strain and in strain rate for muscles of the controlled group. Process 600 then determines (615) muscle activation adjustments based on the changes in muscle strain and in strain rate. Synthesized training data for a reflex controller in accordance with a variety of embodiments of the invention can include desired adjustments for muscle strain and strain rates, as well as muscle activation adjustments associated with the desired adjustments that are computed based on a simulated model.

Although specific methods of synthesizing training data are discussed above, many methods can be implemented in accordance with many different embodiments of the invention. It is therefore to be understood that the present invention may be practiced in ways other than specifically described, without departing from the scope and spirit of the present invention.

In a number of embodiments, sensorimotor control systems can include a torso controller that can be trained in conjunction with controllers for limb complexes and/or for the cervicocephalic complex. Despite the fact that the musculoskeletal complexes of the core (or torso) and each of the 5 extremities include different sets of muscles under the control of different neuromuscular controllers, the force couplings between the extremities and the core can be accomplished in a completely natural manner, through joints and muscles spanning the different musculoskeletal complexes. In numerous embodiments, the articulated biomechanical skeletal structure remains connected while moving. In particular, the spinal joint between the C7 vertebra of the cervical spine and the T1 vertebra of the thoracic spine can apply forces that constrain the cervicocephalic musculoskeletal complex to the torso. At the shoulders, the head of each humerus articulates with the glenoid fossa of its respective scapula in the torso, forming shoulder joints that can apply forces to constrain the arm musculoskeletal complexes to the torso. At the hips, the head of each femur articulates with the acetabulum in the pelvic bone in the torso, forming hip joints that can apply forces to constrain the leg musculoskeletal complexes to the torso.

Further, in numerous embodiments, each of the musculoskeletal complexes of the extremities can include multiple significant muscles that attach to major bones in the torso. These can include the long, superficial muscles of the neck, such as the trapezius; the muscles of the shoulder, such as the biceps, triceps, and the muscles composing the rotator cuff; and the muscles of the hip, such as the gluteal group, adductor group, etc. The virtual counterparts of these muscles exist in the musculoskeletal model in accordance with a number of embodiments of the invention and they can apply common forces between major bones of the torso and the proximal bones of the musculoskeletal complexes of the extremities.

Rather than treating each musculoskeletal complex in isolation and training their motor controllers independently of one another, for viable core training, processes in accordance with various embodiments of the invention can regard the whole-body model as a unified system. Thus, during torso training data synthesis, processes in accordance with several embodiments of the invention can introduce random forces from the extremities onto the torso, such that the torso neuromuscular controller can learn the consequences of forces derived from the extremities. By sending random activation signals to their muscles, the arm, leg, and cervicocephalic complexes can be randomly actuated by modest amounts to synthesize the training data for the torso neuromuscular motor controller. In many embodiments, random activation signals can be sent to the torso muscles as the training data is synthesized for the leg neuromuscular motor controllers. To learn balance, if the center of pressure comes too close to the margin of the support polygon, the biomechanical model is reset to an upright posture and the data synthesis procedure is restarted.

By synthesizing its own training data, virtual humans in accordance with various embodiments of the invention can automatically learn efficient, online, active sensorimotor control of its eyes, head, and limbs in order to perform nontrivial tasks involving the foveation and visual pursuit of target objects coupled with visually-guided limb-reaching actions to intercept the moving targets, as well as to carry out drawing and writing tasks. In numerous embodiments, biomimetic sensorimotor control systems can be capable of performing several nontrivial tasks, including (but not limited to) well-coordinated eye-head movements characteristic of natural active vision, natural limb motions to reach static and kinetic visual targets, and writing and/or drawing by a hand of a model. Experiments have shown that sensorimotor systems that have been trained in accordance with some embodiments of the invention are often capable of generalizing to situations for which they were not specifically trained.

Systems

Figure 7:
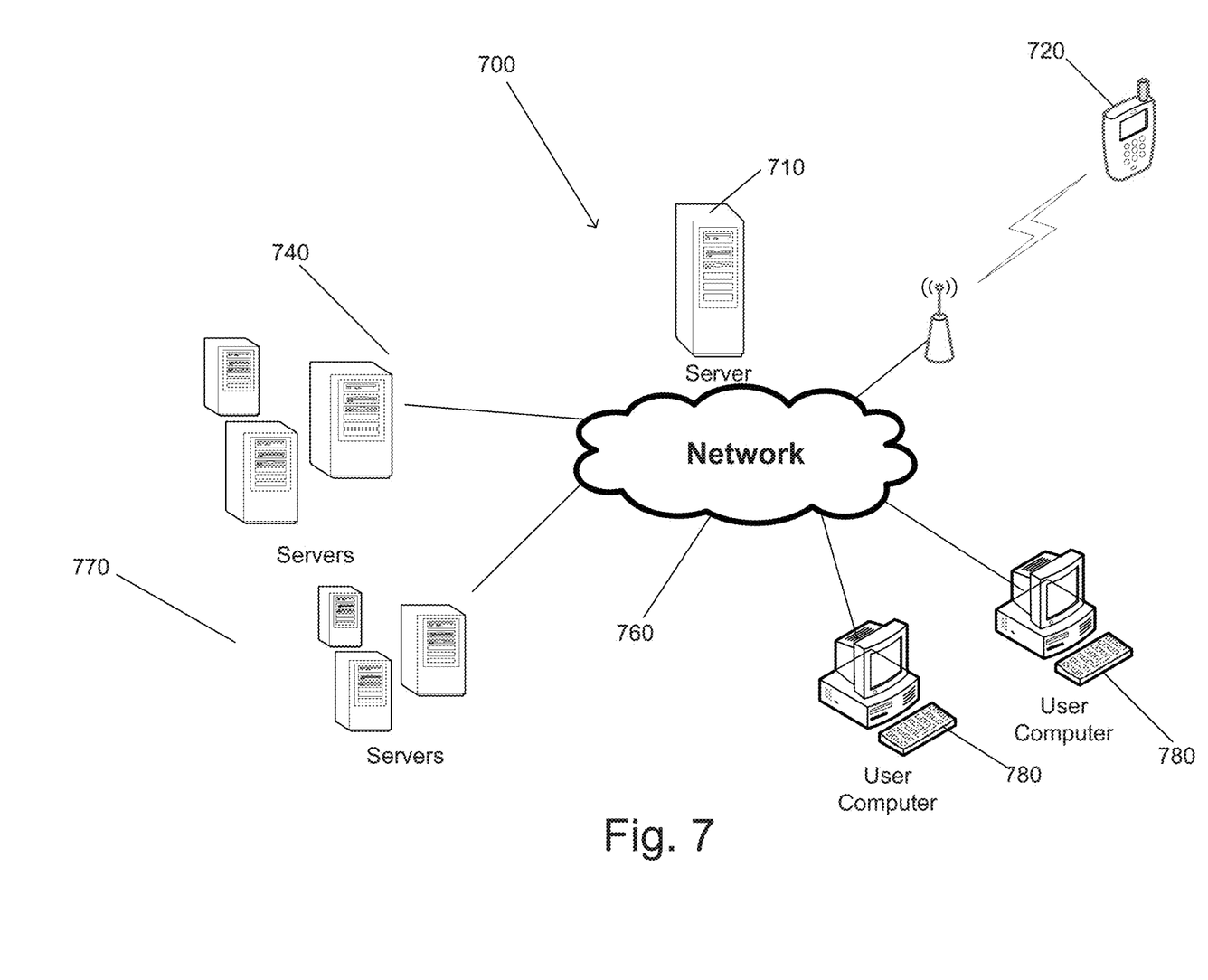
FIG. 7 illustrates an example of a system that trains and implements a sensorimotor control framework in accordance with an embodiment of the invention.

A system that trains and implements a sensorimotor control framework in accordance with an embodiment of the invention is shown in FIG. 7. Network 700 includes a communications network 760. The communications network 760 is a network such as the Internet that allows devices connected to the network 760 to communicate with other connected devices. Server systems 710, 740, and 770 are connected to the network 760. Each of the server systems 710, 740, and 770 is a group of one or more server computer systems communicatively connected to one another via internal networks that execute processes that provide cloud services to users over the network 760. For purposes of this discussion, cloud services are one or more applications that are executed by one or more server systems to provide data and/or executable applications to devices over a network. The server systems 710, 740, and 770 are shown each having three servers connected via an internal network. However, the server systems 710, 740 and 770 may include any number of servers and any additional number of server systems may be connected to the network 760 to provide cloud services including, but not limited to, virtualized server systems. In accordance with various embodiments of this invention, processes for training and/or implementing sensorimotor control frameworks can be provided by one or more software applications executing on a single server system and/or a group of server systems communicating over network 760.

Users may use personal devices 780 and 720 that connect to the network 760 to perform processes for training and/or implementing sensorimotor control frameworks in accordance with various embodiments of the invention. In the illustrated embodiment, the personal devices 780 are shown as desktop computers that are connected via a conventional "wired" connection to the network 760. However, the personal device 780 may be a desktop computer, a laptop computer, a smart television, an entertainment gaming console, or any other device that connects to the network 760 via a "wired" or "wireless" network connection. The mobile device 720 connects to network 760 using a wireless connection. A wireless connection is a connection that uses Radio Frequency (RF) signals, Infrared signals, or any other form of wireless signaling to connect to the network 760. In FIG. 7, the mobile device 720 is a mobile telephone. However, mobile device 720 may be a mobile phone, Personal Digital Assistant (PDA), a tablet, a smartphone, a virtual reality headset, an augmented reality headset, a mixed reality headset or any other type of device that connects to network 760 via wireless connection without departing from this invention. In accordance with some embodiments of the invention, the processes for training and/or implementing sensorimotor control frameworks are performed by the user device. In several other embodiments, an application being executed by the user device may be used to interact with a model and/or to view results of a sensorimotor control framework that is processed by a server system that performs the processes for training and/or implementing sensorimotor control frameworks.

As can readily be appreciated the specific computing system used to train and/or implement sensorimotor control frameworks is largely dependent upon the requirements of a given application and should not be considered as limited to any specific computing system(s) implementation.

Methods

Figure 8:
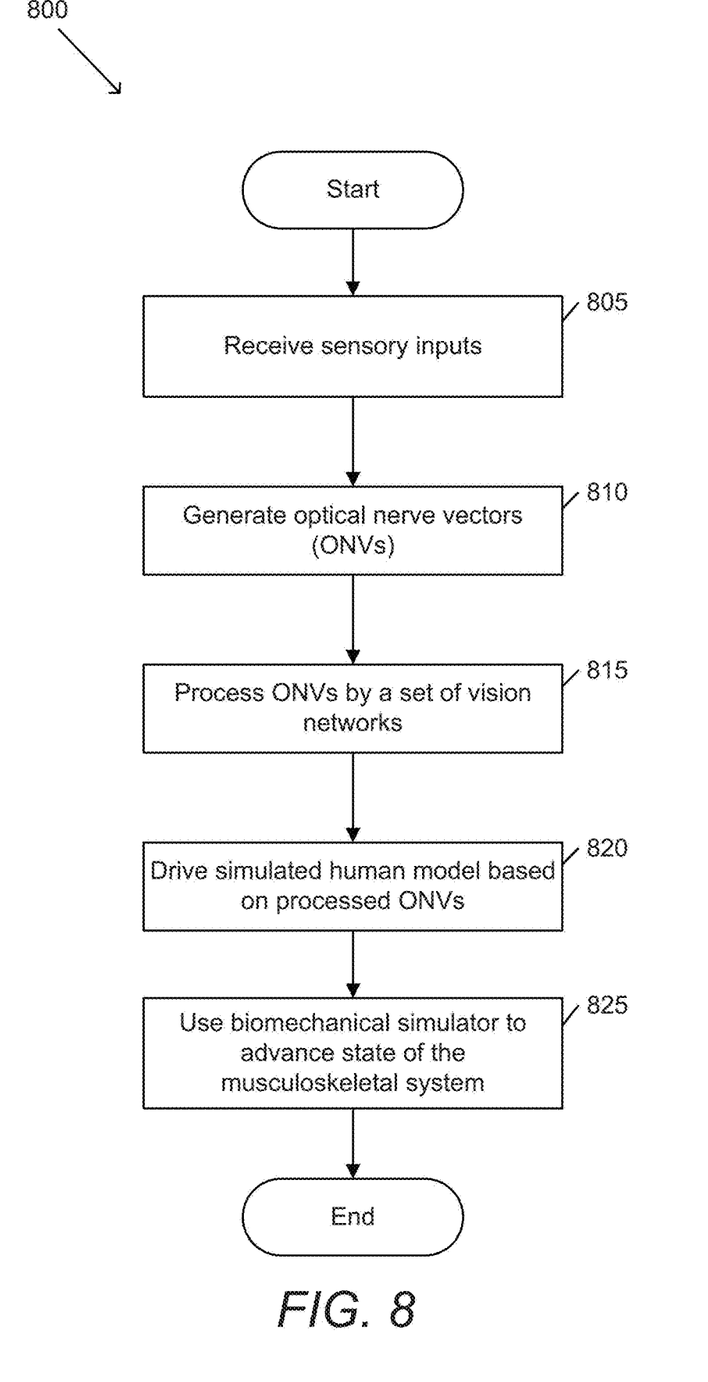
FIG. 8 conceptually illustrates an example of a process for the operation of a sensorimotor control system in accordance with an embodiment of the invention.

An example of a process for the operation of a sensorimotor control system in accordance with an embodiment of the invention is illustrated in FIG. 8. Process 800 receives (805) sensory inputs that can be generated by a sensory element. Sensory outputs in accordance with various embodiments of the invention can include ray traced data for a virtual eye of a simulated human model. Process 800 can optionally generate (810) optic nerve vectors (ONVs) from the received sensory inputs. Process 800 processes (815) the generated ONVs by a set of vision networks. Vision networks in accordance with many embodiments of the invention can include foveation networks and limb vision networks. Process 800 drives (820) the simulated human model based on the processed ONVs. In several embodiments, processes can drive incremental eye rotations that effect saccadic foveation and visual tracking of moving targets. Processes in accordance with many embodiments of the invention can drive the human model by feeding neuromuscular motor controllers, which can produce muscle activation signals for the cervicocephalic and limb musculoskeletal complexes.

Process 800 uses (825) a biomechanical simulator to advance the state of the musculoskeletal system through time, thus incrementally actuating the five complexes subject to external forces, such as gravity. The process can then repeat based on the new states. The three main simulation components can run asynchronously in accordance with a number of embodiments of the invention.

Although specific methods of operating a sensorimotor control system are discussed above, many methods can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A method for operating a sensorimotor control framework, the method comprising:
   determining a current state of a musculoskeletal model comprising a torso complex and a set of one or more limb complexes attached to the torso complex;
   determining a desired state of the musculoskeletal model, wherein the current and desired states comprise at least one of a position, an orientation, a muscle strain, and a strain rate;
   computing forces exerted by the set of limb complexes;
   computing a set of muscle activations for the torso complex, based on the forces exerted by the set of limb complexes and a difference between the current and desired states of the musculoskeletal model; and
   driving a musculoskeletal model based on the computed muscle activations.

2. The method of claim 1, wherein the musculoskeletal model is a model of a human being and comprises a plurality of Hill-type actuators.

3. The method of claim 1, wherein the musculoskeletal model comprises a plurality of complexes, computing the set of muscle activations comprises computing a first set of muscle activations for a first complex and computing a second set of muscle activations for a second complex.

4. The method of claim 3, wherein the plurality of complexes comprises at least one of an arm complex, a leg complex, a cervicocephalic complex, and a torso complex.

5. The method of claim 3, wherein computing the second set of muscle activations for the second complex comprises:
   computing forces from the first set of muscle activations; and
   computing the second set of muscle activations based on the computed forces.

6. The method of claim 1 further comprising receiving sensory inputs from a sensory element, wherein the sensory element is an eye model and the sensory inputs comprise a one-dimensional optic nerve vector (ONV).

7. The method of claim 6, wherein the eye model has a non-uniform distribution of photoreceptors on the retina.

8. The method of claim 1, wherein computing the set of muscle activations comprises:
   computing a voluntary signal using a voluntary controller;
   computing a reflex signal using a reflex controller; and
   computing the set of muscle activations based on outputs from the voluntary controller and outputs from the reflex controller.

9. The method of claim 8, wherein the voluntary controller takes as input a target orientation and output activations for muscles of an associated muscle group.

10. The method of claim 8, wherein the reflex controller takes as input muscle strains and strain rates of muscles of an associated muscle group.

11. A method for training a torso controller of a torso complex, the method comprising:
    receiving training data comprising a set of target inputs and a target state of the torso complex and limb complexes attached to the torso complex;
    determining forces exerted by the limb complexes attached to the torso complex;
    computing muscle activations for the torso complex based on the target inputs, the target state, and the determined forces;
    computing differences between a result of the muscle activations and the target state; and
    modifying parameters of the torso controller based on the differences between the target state and a current state of the torso complex and the limb complexes, wherein the current and target states comprise at least one of a position, an orientation, a muscle strain, and a strain rate.

12. The method of claim 11 further comprising synthesizing the training data.

13. The method of claim 12, wherein synthesizing the training data comprises:
    specifying a current position and a target position for a model;
    determining discrepancies between the current position and the target position;
    determining muscle activation adjustments based on the discrepancies and muscle activations of the current position;
    determining discrepancies comprises solving an inverse kinematics problem.

14. The method of claim 13, wherein the discrepancies comprise at least one of an angular discrepancy, a linear discrepancy, and an acceleration discrepancy.

15. The method of claim 13, wherein determining muscle activation adjustments comprises performing a muscle optimization technique to compute the minimal muscle activations that can generate a desired torque.

16. The method of claim 12, wherein synthesizing the training data comprises:
    specifying current and desired muscle strains and strain rates for a model;
    determining changes in muscle strain and in strain rate for muscles of the controlled group; and
    determining muscle activation adjustments based on the changes in muscle strain and in strain rate.

17. The method of claim 12, wherein determining forces exhibited by limb complexes comprises computing random forces for the set of limb complexes by sending activation signals to the limb complexes.

* * * * *